(12) United States Patent
Birkel et al.

(10) Patent No.: US 6,623,727 B2
(45) Date of Patent: Sep. 23, 2003

(54) SOLID, FORM-STABLE GELS FOR HAIR TREATMENT

(75) Inventors: Susanne Birkel, Darmstadt (DE); Michael Lede, Langen (DE); Juergen Allwohn, Burgschwalbach (DE); Sabine Baecker, Ruesselsheim (DE); Thomas Krause, Darmstadt (DE); Angeliky Beyer, Waldaschaff (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/981,211

(22) Filed: Oct. 17, 2001

(65) Prior Publication Data

US 2002/0076387 A1 Jun. 20, 2002

(30) Foreign Application Priority Data

Oct. 20, 2000 (DE) .......................... 100 51 955

(51) Int. Cl.$^7$ ................................... A61K 7/06
(52) U.S. Cl. ............. 424/70.1; 424/70.13; 424/70.122; 424/70.15; 424/70.16; 424/70.17; 424/74; 424/195.17; 514/944
(58) Field of Search .............................. 424/70.1, 70.13, 424/70.122, 70.15, 70.16, 70.17, DIG. 5, 74, 195.17; 514/944

(56) References Cited

U.S. PATENT DOCUMENTS 5,002,934 A * 3/1991 Norton et al. ................. 514/54
5,843,415 A * 12/1998 Klar .......................... 424/70.1
5,879,669 A * 3/1999 Clausen et al. ........... 424/70.11

FOREIGN PATENT DOCUMENTS

| DE | 37 83 741 T2 | 5/1993 |
| DE | 43 15 405 A1 | 11/1994 |
| DE | 698 00 212 T2 | 11/2000 |
| EP | 0 923 931 A1 | 6/1999 |

OTHER PUBLICATIONS

Skin Care and Cosmetic Ingredients Dictionary, pp. 150 and 154(1994).*

* cited by examiner

Primary Examiner—Jyothsna Venkat
(74) Attorney, Agent, or Firm—Michael J. Striker

(57) ABSTRACT

The solid, form-stable gel for hair treatment contains an aqueous or aqueous-alcoholic base; from 0.5 to less than 2 percent by weight of a carrageenan or a mixture of carrageenans and at least one carrageenan-amount-reducing additive selected from the group consisting of hair fixing polymers, amphiphilic associative thickeners, monoalcohols with 1 to 5 carbon atoms and polyalcohols with 2 to 5 carbon atoms. The carrageenan or mixture of carrageenans and the at least one additive are contained in the gel in respective amounts so that the gel is solid and form-stable, i.e. has a resistance of at least 0.15 N to a compressive force applied at 2000 and 65% relative humidity by means of an 8 mm diameter cylindrical piston that is depressed at a rate of 0.5 mm/s until a compression depth of 1 mm is reached after which the piston is removed at a rate of 0.5 mm/s.

16 Claims, No Drawings

SOLID, FORM-STABLE GELS FOR HAIR TREATMENT

BACKGROUND OF THE INVENTION

1. Field of the Invention

The subject matter of the present invention includes hair treatment compositions in the form of solid, form-stable gels containing carrageenan in an aqueous or aqueous-alcoholic base.

2. Description of the Related Art

Hair treatment compositions, among others, are used in the form a thickened preparations, e.g. gels, in order to fix and hold human hair or to stabilize a prepared hairdo or hairstyle. This type of product has a highly viscous, but still fluid, consistency. These gels are usually packaged in plastic tubes, from which they are forced out in the form of strands when they are used. They usually contain a gel former, such as a polyacrylate, and a hair-fixing polymer, for example polyvinylpyrrolidone. The cosmetic hair-fixing polymers usually used for this purpose in conventional aqueous or aqueous-alcoholic gels have good fixing properties. They hold and fix the hair during application and stabilize an established hairdo or hairstyle.

Because conventional hair gels disadvantageously are not form-stable and deliquesce, it is not possible to proportion them in fixed discrete amounts sufficient for a particular application. Also three-dimensional stability and preparation of an attractive outer form, such as a cube, ball, etc, are not possible. Liquid gels or thixotropic gels, which become liquid under pressure, can run off the hands or the hair during use. An additional disadvantage of the typical carbomer gels is that they only have a stable viscosity in a limited pH range. This means that, in the first place, there is a high production expense because a predetermined pH range must be obtained and, in the second place, there are incompatibilities with other ingredients, which, for their part, can be used only in other pH ranges.

EP 0 923 931 discloses solid cosmetic compositions, which contain at least 2% kappa-carrageenan in combination with certain hydrocolloids in a natural base and which are used essentially as body care sticks (sticks, lipstick). Comparatively large amounts of carrageenan are required in these compositions in order to achieve the required fixing action. These types of compositions are not suitable for hair treatment, since an ugly visible residue forms in the hair because of the large amount of carrageenan included in them (greater than 2% by weight). Sufficient fixing action is no longer obtained when the amount of carrageenan present in the composition is decreased.

SUMMARY OF THE INVENTION

It is an object of the present invention to provide a solid, form-stable gel of the above-described type containing carrageenan for treating hair, which satisfactorily fixes the hair and which can be divided into portions having a stable three-dimensional form during manufacture, and simultaneously is easily and satisfactorily spread with the hands and distributed on the hair.

It is another object of the present invention to provide a solid, form-stable gel of the above-described type for treating hair that includes carrageenan, which satisfactorily fixes the hair and at the same time has a stable viscosity in a wide pH range and forms no undesirable visible residue on the hair.

It has now been found that these objects are attained by a hair treatment composition in the form of a solid, form-stable gel containing a combination of:

(A) a carrageenan or a mixture of carrageenans, and
(B) at least one additive selected from the group consisting of hair fixing polymers, amphiphilic associative thickeners, monoalcohols, polyalcohols, compounds that release calcium ions in aqueous media and compounds that release potassium ions in aqueous media;

in an aqueous or an aqueous-alcoholic base, in which the components (A) and (B) are contained in predetermined amounts, whereby the composition is present in the form of a solid, form-stable gel at room temperature (20° C.).

The words "solid, form-stable", in the sense of the present invention, mean that the gels according to the invention have a resistance to compression under normal conditions (20° C., 65% relative humidity) of at least 0.15 N, preferably from 0.30 to 2.0 N, especially preferably 0.40 to 1.5 N, measured by penetration of the solid gel with a cylindrical piston of a diameter of 8 mm at a penetration speed of 0.5 mm/sec up to a compression depth of 1 mm and subsequently at a withdrawal speed of the piston of 0.5 mm/s. The gels are form-stable at least at room temperature (20° C.) and below, but preferably at temperatures up to 20° C. and especially preferably up to 35° C.

Carrageenan or a mixture of carrageenans and the additive ingredient, which may include a synthetic hair-fixing polymer, are contained in such amounts, that the composition is present at room temperature in the form of a solid, form-stable gel. Normally a carrageenan amount of at least about 3 percent by weight in water is required in order to obtain a solid, form-stable gel, which is unacceptable for hair fixing composition, since it leads to an undesirable residue on the hair. Surprisingly it has been found that it is possible to prepare a hair treatment composition in a solid gel form on the basis of carrageenan, wherein the carrageenan amount is reduced sufficiently so that the undesired residue formed on the hair does not occur. The required solidity of the gel can be achieved, when at least one hair-fixing polymer and/or at least 15% by weight of at least one monoalcohol or polyalcohol and/or at least one salt containing calcium or potassium ion are added.

The composition according to the invention has a sufficient solidity of the gel already with reduced carrageenan amounts (e.g. under 2 percent by weight). It is thus possible to use the composition for hair treatment, especially by addition of hair fixing polymers as hair styling agents for hair fixing, since the problem of the undesired residue formation is thus solved.

Carrageenan

Carrageenan, especially kappa-carrageenan or iota-carrageenan, is suitable as a gel-former in the composition according to the invention. Kappa-carrageenan or a carrageenan mixture containing kappa-carrageenan is particularly preferred. For example, a carrageenan with an average molecular weight like that in SEA KEM® CM 611 of FMC Corporation, which is a mixture of carrageenan and dextrose, is especially well suited for the compositions according to the invention. The gel-former is used in those amounts, so that the composition is present in the form of a solid, form-stable gel at room temperature (20° C.). The carrageenan is suitably present in the composition according to the invention e.g. in an amount of from 0.5 to 5 percent by weight, preferably from 1 to less than 2.5 percent by weight and especially preferably from 1.3 to less than or equal to 2 percent by weight. The solidification of the gel can take place after some time, i.e. in the course of two to three days. The hardening of the gel however can be accelerated if the gel-former is first dissolved in water, if necessary, with heating at about 80° C. and subsequently is rapidly cooled to at least 50 to 55° C. with additional external cooling.

Calcium and Potassium Ions

The at least one additive in the gels according to the invention also may be calcium and/or potassium ions that are released by water-soluble compounds included in the aqueous or aqueous-alcoholic base. These water-soluble compounds are preferably water-soluble salts, e.g. halogenides, sulfates, etc, of which the chlorides are especially preferred. Preferably these water-soluble salts are included in the compositions of the invention in an amount of from 0.2 to 1 percent by weight, especially preferably from 0.4 to 0.8 percent by weight. Potassium ions are preferred, since clear non-turbid gels are produced when the gels include the potassium ions.

Hair-Fixing Polymers

It has been shown that the solid gel with pure carrageenan has a certain hair fixing action, even without additional conventional hair-fixing polymers. In this case however for sufficient hair fixing comparatively large amounts of carrageenan are required, which leads to the undesirable side effect comprising the visible residue on the hair. When the amount of carrageenan is lowered, the hair fixing action is no longer sufficient and also the solidity and form-stability of the gel is lost. The gel according to the invention that contains at least one additional synthetic or natural hair-fixing polymer will provide sufficient hair fixing without the undesirable side effects or at least with reduced side effects.

The additional hair-fixing polymer, when present, is included in the composition of the invention in an amount of from 0.1 to 30 percent by weight, especially preferably from 0.5 to 15 percent by weight. The hair-fixing polymer can be non-ionic, anionic, zwitterionic or amphoteric. Polymers, which do not contain cationic groups, i.e. anionic, nonionic and amphoteric polymers, are particularly preferred. Synthetic polymers are understood to be those polymers, which have a purely synthetic, i.e. not natural origin, especially those, which are made by radical polymerization from ethylenic unsaturated monomers or by polycondensation. Those polymers are particularly preferred, which have sufficient solubility or dispersibility in water, alcohol or alcohol/water mixtures, in order to be present in dissolved or uniformly dispersed form in compositions according to the invention on an aqueous basis. "Hair-fixing polymers" are understood to be those polymers, which, when used in an amount of from 0.01 to 5% in an aqueous, alcoholic or aqueous-alcoholic solution, are in a position to deposit a polymer film on the hair and to fix the hair.

Nonionic, anionic or amphoteric film-forming hair-fixing polymers are especially preferred in the gels according to the invention. Suitable non-ionic polymers include homopolymers or copolymers, which are built up from at least one of the following monomers: vinylpyrrolidone, vinylcaprolactam, vinyl esters such as vinyl acetate, vinyl alcohol, acrylamide, methacrylamide, alkyl- and dialkylacrylamide, alkyl- and dialkylmethacrylamide, alkylacrylate, alkylmethacrylate, propylene glycol or ethylene glycol, wherein the alkyl groups in these monomers preferably have from one to seven carbon atoms, especially preferably from one to three carbon atoms. For example, homopolymers of vinyl caprolactam, of vinyl pyrrolidone or of N-vinylformamide, are especially suitable. Additional suitable synthetic non-ionic film-forming hair-fixing polymers are e.g. copolymerizateS of vinyl pyrrolidone and vinyl acetate, terpolymers of vinyl pyrrolidone, vinyl acetate and vinyl propionate, polyacrylamide, which, for example, are sold under the trade name AKYPOMINE® P 191 of CHEM-Y, Emmerich, Germany, or SEPIGEL® 305 of SEPPIC, USA; polyvinyl alcohols, which, for example, are marketed under the trade name ELVANOLe of DuPont or VINOL® 523/540 of Air Products, U.S.A., and polyethylene glycol/ polypropylene glycol copolymers, which are sold e.g. under the trademark UCON® of Union Carbide. Polyvinyl pyrrolidone, polyvinyl caprolactam and their copolymers with at least one additional non-ionic polymer, especially polyvinyl pyrrolidone/vinyl acetate copolymers are especially preferred.

Suitable anionic hair-fixing polymers include synthetic homo- or copolymers with neutralizable monomer units containing acid groups, which are copolymerizable with comonomers, if necessary, which contain no acid groups. The acid groups may include —COOH, —SO$_3$H, —OSO$_3$H, —OPO$_2$H and —OPO$_3$H groups, of which the carboxylic acid groups are especially preferred. The anionic polymers in the composition according to the invention are partially or completely neutralized with a cosmetically compatible neutralizing agent. They are present in the composition according to the invention in a form that is 50% neutralized or in a completely neutralized form. Organic or inorganic bases can be used as the neutralizing agent. For example, suitable bases include, especially, aminoalkanols, such as aminomethylpropanol (AMP), triethanolamines or monoethanolamines, however ammonia, NaOH, among others, are also suitable. Suitable monomers include unsaturated, radically polymerizable compounds, which have at least one acid group, especially carboxyvinyl monomers. Suitable monomers including acid groups are, e.g., acrylic acid, methacrylic acid, crotonic acid, maleic acid and/or maleic acid anhydride or their monoesters.

Comonomers not substituted with acid groups include, e.g., acryl amide, methacrylamides, alkyl and dialkylacrylamides, alkyl and dialkylmethacrylamides, alkylacrylates, alkylmethacrylates, vinyl caprolactone, vinyl pyrrolidone, vinyl esters, vinyl alcohol, propylene glycol or ethylene glycol, amine-substituted vinyl monomers, such as dialkylaminoalkylacrylates, dialkylaminoalkylmethacrylates, monoalkyl-aminoalkylacrylates and monoalkylaminoalkylmethacrylates, in which the alkyl groups of these monomers preferably contain one to seven carbon atoms, especially preferably from one to three carbon atoms.

Suitable polymers with acid groups include especially copolymers of acrylic acid or methacrylic acid with monomers selected from the group consisting of acrylic acid or methacrylic acid esters, acryl amides, methacrylamides and vinylpyrrolidones, homopolymers of crotonic acid and copolymers of crotonic acid with monomers selected from the group consisting of vinyl esters, acrylic acid or methacrylic acid esters, acrylamides and methacrylamides. A suitable natural polymer is, for example, shellac.

Preferred polymers with acid groups include cross-linked or uncross-linked vinyl acetate/crotonic acid copolymers. Similarly partially esterified copolymers between vinyl methyl ether and maleic acid anhydride are also preferred. Additional preferred anionic polymers include, e.g., terpolymers of acrylic acid, alkyl acrylate and N-alkylacrylamide, especially acrylic acid/ethyl acrylate/N-t-butylacrylamide terpolymer, terpolymers of vinyl acetate, crotonate and vinyl alkanoate, especially vinyl acetate/crotonate/vinyl neodecanoate copolymers, and copolymers of acrylic acid or methacrylic acid and acrylic acid alkyl esters or methacrylic acid alkyl esters, wherein the alkyl groups preferably contain from one to seven carbon atoms.

Suitable amphoteric hair-fixing polymers are those polymers, which contain basic or cationic groups as well as acidic or anionic groups as additional functional groups. The basic or cationic groups are, for example, primary, secondary and tertiary amine groups. For example, suitable amphoteric polymers are, for example, copolymers made from alkylacrylamides (especially octylacrylamide), alkylaminoalkylmethaclylates (especially t-butylaminoethylmethacrylate), and two or more monomers, comprising acrylic acid, methacrylic acid or their esters, such as those which are obtainable under the trademarks AMPHOMER® and AMPHOMER® LV-71 of National Starch, U.S.A. Further examples of suitable copolymers include those copolymers of acrylic acid, methacrylate and methacrylamideoPrOPYltrimethylammonium chloride (INCI: poIyquaternium-47), which are sold under the trade name MERQUAT® 2001 of Calgon, Pittsburgh, U.S.A., those copolymers made from acrylamidopropyltrimethyl ammonium chloride and acrylates, such as those sold under the trademark W 37194® by Stockhausen or those copolymers made from acrylamide, acrylamidopropyltrimethylammonium chloride, 2-amidopropylacrylamide sulfonate and dimethylaminopropylamine (DMAPA)(INCI: Polyquaternium-43), such as those marketed under the trademark BOZEQUAT® 4000 of Societe Francaise Hoechst. Suitable polymers made with monomers carrying betaine groups, such as copolymers of methacryloylethylbetaine and two or more monomers made from acrylic acid or their simple esters, known under the INCI designation methacryloyl ethyl betaine/acrylates copolymer.

Aqueous or Aqueous-Alcoholic Base

The gel according to the invention is preferably packaged in an aqueous base. The aqueous base can be either a purely aqueous medium or an aqueous-alcoholic medium with preferably up to 40 percent by weight alcohol. Lower univalent or multivalent alcohols suitable for cosmetic purposes and having from one to five carbon atoms, such as, e.g., ethanol, isopropanol, ethylene glycol, glycerol and propylene glycols, especially 1,2-propylene glycol, may be used as the alcohol. Typical water content is from 55 to 95 percent by weight and preferably from 65 to 80 percent by weight. Typical alcohol content is from 0 to 30 percent by weight and preferably from 1 to 25 percent by weight. There is a danger that carrageenan will precipitate when the alcohol content is over 40 percent by weight.

The use of at least 15 percent by weight alcohol is especially preferred, since sufficient solidity or hardness and form-stability of the gel can be achieved already with carrageenan amounts of less than the otherwise required at least 2.5 to 3 percent by weight, especially with less than 2 percent by weight. Moreover an additional preservative is not absolutely required when at least 15 percent by weight of the alcohol is used.

A special advantage of the gel according to the invention is that the viscosity is stable over a wide pH range of from 1 to 14. A pH range of from 2.5 to 8 is especially preferred.

Preservative

Since the carrageenan used in the gel according to the invention is a polymer of natural origin based on saccharides, special requirements are established for preserving the composition according to the invention in order to guarantee longer storage stability. Parabenes, especially methylparabene, has proven to be suitable as the preservative. With an ethanol content of about 15 percent by weight or more an additional preservative is not absolutely required.

Sugar

The composition according to the invention contains at least one sugar in order to improve the clarity and transparency of the composition according to the invention Suitable sugars, for example, include monosaccharides and disaccharides, such as glucose, galactose, fructose, maltose, lactose or saccharose. Typically from 0.01 to 5, preferably 0.05 to 1, percent by weight, of sugar is used in the composition according to the invention. Preferably mixtures of carrageenan and sugar, such as the raw material, SEA KEM® CM 611, are preferred. This latter raw material is a mixture of carrageenan and dextrose.

Additive Ingredients for Improved Spreadability and Distributability

The composition according to the invention preferably contains additional thickeners or gel-formers to improve the spreadability of the product on the hands and/or the distributability of the product in the hair. Carboxy polymers, especially polyacrylates, such as the different carbopol types, polyglycols also, cellulose derivative compounds, especially hydroxyalkyl cellulose compounds and inorganic thickeners, such as natural or synthetic bentonites. Typical concentrations of the additional gel-formers and thickeners are from about 0.2 to 10.0 percent by weight, preferably from 1 to 5 percent by weight.

Suitable substances, which facilitate spreading the gel or distributing the gel in the hair, include xanthene gum and cellulose derivative compounds, such as those described in EP 0 923 931. These compounds are hydrocolloids, especially carboxymethyl cellulose and hydroxyethyl cellulose, which are soluble in hot water.

Surprisingly it has been found that solid gels based on carrageenan are particularly well spread and distributed when amphiphilic associative thickeners are used in them. Suitable amphiphilic associative thickeners include nonionic polymers, which contained both hydrophilic and hydrophobic groups. Associative thickeners are water-soluble polymers and have surfactant-like hydrophobic groups, which are in a position to associate with themselves and also with other hydrophobic materials, in a hydrophilic, especially aqueous, medium, i.e. in a reciprocal interaction. The medium thickens or gels because of the resulting associative network. Typically associative thickeners are made by polymerization of polyethylene oxide pre-polymers and at least bifunctional, polycondensible substances, such as isocyanates, to obtain monols or diols with large built-in aryl-, alkyl- or aryl/alkyl groups, to provide a hydrophobic modification. Hydrophobically modified polyalkylene glycols are thus preferred associative thickeners. In these associative thickeners the hydrophilic part is provided by polyoxyalkylene units, preferably polyoxyethylene units, but also polyoxypropylene units or their mixtures. Hydrocarbon groups, e.g. long-chain alkyl groups, alkylaryl groups or arylalkyl groups, preferably form the hydrophobic part of the associative thickeners.

Hydrophobically modified aminoplast-polyether copolymers are especially preferred as the associative thickener ingredient. Their structure and manufacturing methods are described in WO 96/40815 and incorporated here by reference. Water-dispersible or water-soluble copolymers are described in WO 96/40815. These latter copolymers are reaction products of an acid catalyzed polycondensation of at least bifunctional aminoplast monomers and at least bifunctional alkylene polyethers and simple functional compounds with hydrophobic groups. Suitable aminoplasts are shown in FIG. 1 of WO 96/40815. The glycoluril derivative compounds of formula X of WO 96/40815 are especially preferred. Suitable alkylene polyethers are disclosed in FIG. 2 of WO 96/40815. Polyethylene oxide diols are preferred alkylene polyethers. They can have an ethylene oxylation degree of from 20 to 500, preferably from 50 to 350, especially preferably from 100 to 250. Suitable simple functional compounds groups with hydrophobic groups are those of formula XIV of WO 96/40815.

Suitable associative thickeners according to the invention are those selected from the polymers of the general formula (I):

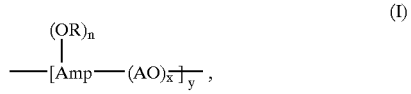

wherein amp means an aminoplast monomer or a group of an aminoplast oligomer or an aminoplast polymer, AO represents an alkylene oxide group, R represents hydrogen, $C_1$-to $C_4$-alkyl or $C_1$-to $C_4$-acyl, x and y are numbers greater than 1 and n is a positive number, which corresponds to the number of the free valences of Amp. The reaction products of acid catalyzed polycondensates of (a) glycolurils of the general formula (II),

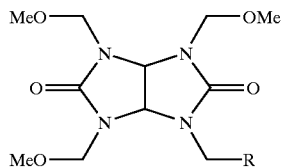

wherein R represents H or preferably OMe, (b) polyethylene oxide diols of an ethoxylation degree of 20 to 500, preferably from 50 to 350, especially preferably from 100 to 250, and (c) ethoxylated, as needed, hydrophobic alcohols, alkyl phenols, thiols, carboxamides, carbamates or hydrophobic carboxylic acids, as described on pages 17 to 19 of WO 96/40815 are particularly preferred. 1,3,4,6 tetramethoxymethylglycol-uril is especially preferred as the glycoluril.

Suitable associative thickeners are those with the INCI names, polyether-1, PEG-180/Octoxynol-40/TMMG copolymer and PEG-180/Laureth-50/TMMG copolymer. Polyether-1 is marketed under the trademark, PURE THIX® HH or PURE THIX® TX 1442 by Süd-Chemie. S üd-Chemie also markets PEG-180/Octoxynol-40/TMMG copolymer under the trademark PURE THIX® L and PEG-180/Laureth-50/TMMG copolymer under the trademark PURE THIX® M.

Optional Additive Ingredients

The compositions according to the invention can also contain conventional additive ingredients suitable for hair treatment compositions. These additive ingredients include, e.g. wetting agents or emulsifiers in an amount of from 0.1 to 15 percent by weight; moisturizers; perfume oils in an amount of 0.1 to 0.5 percent by weight; bactericidal and fungicidal agents, for example, 2,4,4 trichloro-2-hydroxydiphenyl ether or methyl chloroisothiazolione, in an amount of from 0.01 to 1.0 percent by weight; buffer substances, such as sodium citrate or sodium phosphate, in an amount of from 0.1 to 1.0 percent by weight; dyestuffs, for example, fluorescein sodium salt, in an amount of about 0.1 to 1.0 percent by weight; care materials, such as plant and vegetable extracts, protein and silk hydrolyzates, lanolin derivative compounds, in an amount of 0.1 to 5 percent by weight, physiologically compatible silicone derivative compounds, such as volatile or non-volatile silicone oils or high-molecular-weight siloxane polymers in an amount of from 0.05 to 20 percent by weight; light protective materials, antioxidants, radical trapping agents, anti-flaking active ingredients, in an amount of about 0.01 to 2 percent by weight; luster-imparting ingredients, vitamins, softening agents, combability improving agents and de-fatting agents.

Preparation Process

The compositions according to the invention can be made by a process in which the carrageenan (A) and additional hair cosmetic additive and auxiliary ingredients are first dissolved in an aqueous solvent. The amount of the gel-former and the type and the amount of the additional cosmetic additive ingredients are selected so that a solid, form-stable gel can be formed. In the event that the gel-former or the additional additive ingredients are not completely soluble at room temperature, heat can be used to dissolve those materials, e.g. at about 40 to 80° C. Then the resulting solution is allowed to stand until the solution solidifies to form the gel. Advantageously additional external cooling at least 50 to 55° C. or lower accelerates the solidification process.

The composition according to the invention is characterized by being dividable into non-deliquescent stable, three-dimensional shapes or forms at room temperature (20° C.). Suitable three-dimensional portions or shapes include, e.g. cubes, parallelepipeds, balls, eggs, hearts, alphabetic or numerical characters, logos, animal body forms, star shapes or other mini sculptures. These shapes can be made when a heated, still-flowing gel composition is cast or molded in a suitable mold and cooled. Also they can be made by cutting them out of a larger block by means of a suitable cutting tool or by punching them out with a suitable punching tool.

A preferred process for forming three dimensional gel bodies or portions includes pressing the desired predetermined shape for the gel portions into a suitable receiving material with a piston or pressing tool to form a mold. The mold for the gel bodies or portions is formed by pressing the desired shapes for the gel bodies or portions into starch material. This starch material can be a conditioned starch powder, a hydrophobic starch powder or a paste of grain meal, e.g. corn meal. Then the still fluid gel mass is cast in the mold made from starch powder. After a standing time sufficient for solidification of the gel mass, the starch powder is removed, for example, by screening or sifting, blowing, washing or taking out the solid gel portion from the mold. The articles preferably are surface-treated subsequently for producing a lustrous surface and to avoid sticking to each other. The article can be sprayed with steam or rinsed with glycerol or with silicone oils and subsequently dried. Also the article can be coated on its surface with fats or waxes, for example bees wax.

The following examples illustrate the subject matter of the invention in more detail, without limiting the broad concept of the invention as expressed in the appended claims. The polymer content disclosed in the examples relates to the solid content.

EXAMPLES

The ingredients disclosed in the following recipes are dissolved in the respective solvent with heating at about 70° C. In a first process for forming or shaping the resulting solution is allowed to cool on standing to room temperature so that the get solidifies. The solid gels are divided into portions by cutting the solidified gel with a knife to form stable cubes or parallelpipeds.

In an alternative second process for molding a beaker or other vessel is filled with hydrophobic starch powder (DRY FLO® PC of National Starch). Round depressions are formed or pressed into the starch powder. The still fluid gel composition is poured into the depressions and subsequently allowed to cool. After solidification the solid gel pellets are taken from the starch powder, screened and rinsed off with glycerol or silicone oil, especially phenyl trimethicone (BAYSILON® PD5). The gel pellets are coated with beeswax to heighten their luster. The solid gel articles are also form-stable at 40° C. during storage for two weeks.

Example 1

Gel 1.5 g SEA KEM® CM 611 (Carrageenan and Dextrose, FMC Corp.)
2.5 g LUVISET® CA 66 (Vinyl acetate/crotonic acid copolymer, BASE)
0.26 g Aminomethyipropanol (95%)
2.5 g PURE THIX® TX 1442 (Polyether-1, Süd-Chemie(South Chemical), United Catalysts)
20 g Ethanol
to 100 g Water

Example 2

Gel with Lighter Solids 1.5 g SEA KEM® CM 611 (Carrageenan and Dextrose, FMC Corp.)
2.0 g Special shellac SSB® 63 HE-N (Stroever GmbH & Co. KG)
2.5 g PURE THIX® TX 1442 (Polyether-1, SQd-Chem,e(SOUth Chemical), United Catalysts)
19.0 g Ethanol
0.3 g Perfume
0.2 g PEG-40 Hydrogenated castor oil
0.2 g PPG-1-PEG-9 Lauryl glycol ether
0.5 g PEG-25 PABA
to 100 g Water

Example 3

Gel with Heavier Solids 1.9 g SEA KEM® CM 611 (Carrageenan and Dextrose, FMC Corp.)
3.5 g Octylacrylamide/acrylates/butylaminoethylmethacrylate Copolymer (AMPHOMER
0.6 g AminomethylpropaflOl (95%)
0.1 g Carbomer
0.95 g NaOH, 5%
19.0 g Ethanol
0.3 g Perfume
0.2 g PEG-40 Hydrogenated castor oil
0.2 g PPG-1-PEG-9 Lauryl glycol ether
0.3 g Panthenol
to 100 g Water

Example 4

Fast-Drying Gel 1.4 g SEA KEM® CM 611 (Carrageenan and Dextrose, FMC Corp.)
2.5 g Vinyl acetate/crotonate copolymer (LUVISET® CA 66)
0.26 g Aminomethylpropanol (95%)
0.2 g Hydroxyethylcellulose
29.0 g Ethanol
0.3 g Perfume
0.4 g PEG-40 Hydrogenated castor oil
to 100 g Water

Example 5

Wet-Look Gel 1.7 g SEA KEM® CM 611 (Carrageenan and Dextrose, FMC Corp.)
2.5 g PURE THIX® TX 1442 (polyether-1, Süd-Chemie (South Chemical), United Catalysts)
10.0 g Propylene glycol
10.0 Ethanol
0.3 g Perfume
0.2 g PEG-40 Hydrogenated castor oil
0.2 g PPG-1 PEG-9 lauryl glycol ether
0.3 g Methyl parabene
0.02 g Mica
to 100 g Water The percentages by weight recited in the appended claims are all based on the total weight of the composition, i.e. the gel.

The disclosure in German Patent Application 100 51 955.5-42 of Oct. 20, 2000 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in solid, form-stable gels for hair treatment, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A solid, form-stable gel for hair treatment comprising an aqueous or aqueous-alcoholic base;
from 0.5 to less than 2 percent by weight of a carrageenan mixture containing kappa-carrageenans; and
at least one additive selected from the group consisting of hair fixing polymers, amphiphilic associative thickeners, monoalcohols with 1 to 5 carbon atoms and polyalcohols with 2 to 5 carbon atoms;
wherein said amphiphilic associative thickeners, when included in said at least one additive, are contained in an amount of from 0.2 to 10 percent by weight; said monoalcohols, when included in said at least one additive, are contained in an amount of at least 15 percent by weight; said polyalcohols, when included in said at least one additive, are contained in an amount of at least 15 percent by weight; and said hair fixing polymers, when included in said at least one additive, are contained in an amount of from 0.5 to 30 percent by weight; and wherein said carrageenan mixture containing kappa-carrageenan and said at least one additive are contained in the gel in respective amounts such that the gel is solid and form-stable and has a resistance of at least 0.15 N to a compressive force applied at 20° C. and 65% relative humidity by means of a cylindrical piston of a diameter of 8 mm that is depressed at a rate of 0.5 mm/s until a compression depth of 1 mm is reached after which the piston is removed at a rate of 0.5 mm/s.

2. The gel as defined in claim 1, wherein said at least one additive is an anionic hair fixing polymer, a non-ionic hair fixing polymer or an amphoteric hair fixing polymer.

3. The gel as defined in claim 2, wherein said at least one additive is selected from the group consisting of cross-linked vinyl acetate/crotonic acid copolymers; uncross-linked vinyl acetate/crotonic acid copolymers; partially esterified copolymers of vinyl methyl ether and maleic acid anhydride; terpolymers of acrylic acid, alkyl acrylates and N-alkylacrylamides; terpolymers of vinyl acetate, crotonates and vinyl alkanoate; copolymers of acrylic acid and acrylic acid alkyl esters; copolymers of acrylic acid and methacrylic acid alkyl esters; copolymers of methacrylic acid and acrylic acid alkyl esters; copolymers of methacrylic acid and methacrylic acid alkyl esters; polyvinyl pyrrolidones; vinylpyrrolidone/vinyl acetate copolymers and copolymers of alkyl acrylamides, alkylaminoalkyl-methacrylates and two or more monomers; and wherein said monomers are selected from the group consisting of acrylic acid, methacrylic acid, esters of acrylic acid and esters or methacrylic acid, and wherein at least one of said two or more monomers contains an acid group, and wherein each of said alkyl is a group with one to seven carbon atoms.

4. The gel as defined in claim 1, containing from at least 1 percent by weight to less than 2 percent by weight of said carrageenan mixture containing kappa-carrageenan and from 0.5 to 15 percent by weight of at least one of said hair-fixing polymers.

5. The gel as defined in claim 1, containing said aqueous-alcoholic base and wherein said at least one additive is selected from the group consisting of ethanol, isopropanol, ethylene glycol, glycerol and propylene glycol.

6. The gel as defined in claim 1, free of a preservative ingredient besides said monoalcohols or said polyalcohols when said at least one additive includes one of said monoalcohols or said polyalcohols.

7. The gel as defined in claim 1, containing at least one of said hair-fixing polymers.

8. The gel as defined in claim 1, further comprising at least one substance for improving spreadability of the gel or the distributability of the gel and wherein said at least one substance is selected from the group consisting of said amphiphilic associative thickeners, xanthene gum and cellulose derivative compounds.

9. The gel as defined in claim 1, containing at least one of said amphiphilic associative thickeners.

10. The gel as defined in claim 9, containing at least one of said hair-fixing polymers.

11. The gel as defined in claim 9, wherein said amphiphilic associate thickener is selected from the group consisting of polyether-1, PEG-180/Octoxynol-40/TMMG copolymers and PEG-180/Laureth-50/TMMG copolymers.

12. The gel as defined in claim 1, further comprising at least one sugar.

13. The gel as defined in claim 12, wherein said at least one sugar is selected from the group consisting of glucose, galactose, fructose, maltose, lactose and saccharose.

14. The gel as defined in claim 1, in the format a plurality of cubes, parallelepipeds, eggs, hearts, characters, logos, animal body forms or stars.

15. A process for making a plurality of three-dimensional bodies for hair treatment, said process comprising the steps of:
   a) forming respective molds for the three dimensional bodies by pressing corresponding predetermined shapes into a starch material;
   b) pouring a still fluid gel mass into said respective molds;
   c) after the pouring of step b), allowing said fluid gel mass in said respective molds to cool until said gel mass solidifies; and
   d) removing said starch material from said gel mass after solidification to form said three dimensional bodies in said predetermined shapes;
   wherein said gel mass comprises an aqueous or aqueous-alcoholic base;
   from 0.5 to less than 2 percent by weight of a carrageenan mixture containing kappa-carrageenans; and
   at least one additive selected from the group consisting of hair fixing polymers, amphiphilic associative thickeners, monoalcohols with 1 to 5 carbon atoms and polyalcohols with 2 to 5 carbon atoms;
   wherein said amphiphilic associative thickeners when included in said at least one additive, are contained in an amount of from 0.2 to 10 percent by weight; said monoalcohols, when included in said at least one additive, are contained in an amount of at least 15 percent by weight; said polyalcohols, when included in said at least one additive, are contained in an amount of at least 15 percent by weight; and said hair fixing polymers, when included in said at least one additive, are contained in an amount of from 0.5 to 30 percent by weight; and
   wherein said carrageenan mixture containing kappa-carrageenan and said at least one additive are contained in respective amounts such that the gel is solid and form-stable and has a resistance of at least 0.15 N to a compressive force applied at 20° C. and 65% relative humidity by means of a cylindrical piston of a diameter of 8 mm that is depressed at a rate of 0.5 mm/s until a compression depth of 1 mm is reached after which the piston is removed at a rate of 0.5 mm/s.

16. The process as defined in claim 15, wherein said starch material is selected from the group consisting of a conditioned starch powder, a hydrophobic starch powder and a grain meal paste.

* * * * *